(12) United States Patent
Ceriani et al.

(10) Patent No.: US 6,527,733 B1
(45) Date of Patent: Mar. 4, 2003

(54) HINGE ASSEMBLY FOR AN ORTHOPEDIC KNEE BRACE AND KNEE BRACE INCORPORATING THE HINGE ASSEMBLY

(75) Inventors: Dylann D. Ceriani, San Diego, CA (US); Theodore V. Tillinghast, Cardiff, CA (US); Richard E. Gildersleeve, Escondido, CA (US); Scott P. Seligman, Carlsbad, CA (US)

(73) Assignee: DJ Orthopedics, LLC, Vista, CA (US)

( * ) Notice: Subject to any disclaimer, the term of this patent is extended or adjusted under 35 U.S.C. 154(b) by 0 days.

(21) Appl. No.: 09/510,397

(22) Filed: Feb. 22, 2000

(51) Int. Cl.7 .................................................. A61F 5/00
(52) U.S. Cl. ........................................ 602/16; 602/26
(58) Field of Search .............................. 602/5, 16, 23, 602/26; 128/869, 882

(56) References Cited

U.S. PATENT DOCUMENTS

| | | | |
|---|---|---|---|
| 4,256,097 A | 3/1981 | Willis | |
| 4,632,098 A | 12/1986 | Grundei et al. | |
| 4,803,975 A | 2/1989 | Meyers | |
| 4,881,532 A | 11/1989 | Borig et al. | |
| 4,940,044 A | 7/1990 | Castillo | |
| 4,986,264 A | 1/1991 | Miller | |
| 5,039,247 A | 8/1991 | Young et al. | |
| 5,086,760 A | 2/1992 | Neumann et al. | |
| 5,277,698 A | 1/1994 | Taylor | |
| 5,302,169 A | 4/1994 | Taylor | |
| 5,358,469 A | * 10/1994 | Patchel ......................... | 602/26 |
| 5,399,149 A | 3/1995 | Frankowiak et al. | |
| 5,419,754 A | * 5/1995 | Hutchins ...................... | 602/26 |
| 5,421,810 A | 6/1995 | Davis et al. | |
| 5,458,565 A | 10/1995 | Tillinghast, III et al. | |
| 5,558,627 A | 9/1996 | Singer et al. | |
| 5,586,970 A | 12/1996 | Morris et al. | |
| 5,645,524 A | * 7/1997 | Doyle .......................... | 602/26 |
| 5,669,873 A | 9/1997 | Towsley | |
| 5,743,865 A | 4/1998 | Townsend | |
| 5,766,140 A | 6/1998 | Tillinghast, III et al. | |
| 5,792,086 A | 8/1998 | Bleau et al. | |
| 5,807,294 A | 9/1998 | Cawley et al. | |
| 5,814,000 A | 9/1998 | Kilbey | |
| 5,860,943 A | 1/1999 | Bloedau et al. | |
| 6,001,075 A | * 12/1999 | Clemens ....................... | 602/16 |

FOREIGN PATENT DOCUMENTS

| | | |
|---|---|---|
| GB | 2136294 | 3/1983 |
| GB | 2163352 | 1/1985 |

* cited by examiner

*Primary Examiner*—Michael A. Brown
(74) *Attorney, Agent, or Firm*—Knobbe, Martens, Olson & Bear, LLP (57) ABSTRACT

A hinge assembly is provided for an orthopedic knee brace. The knee brace includes upper and lower support arms. The hinge assembly includes a hinge plate and first and second gear members pivotally connected to the hinge plate. The first gear member is coupled for rotation with the upper support arm and has an articulation surface adjacent a surface of the upper support arm. The second gear member is coupled for rotation with the lower support arm and has an articulation surface adjacent a surface of the lower support arm. The hinge assembly allows medial/lateral articulation of the upper and lower support arms in a plane substantially perpendicular to a plane of rotation of the first and second gear members.

17 Claims, 11 Drawing Sheets

HINGE ASSEMBLY FOR AN ORTHOPEDIC KNEE BRACE AND KNEE BRACE INCORPORATING THE HINGE ASSEMBLY

BACKGROUND OF THE INVENTION

1. Field of the Invention

The present invention relates generally to orthopedic braces and, in particular, to orthopedic knee braces.

2. Description of the Related Art

Osteoarthritis is a degenerative joint disease that results in chronic pain in an affected joint when the joint is statically or dynamically loaded. In an affected knee joint, osteoarthritis pain is often caused by an unbalanced loading on the medial or lateral compartment of the knee, which can reduce the clearance space between the condyles of the femur and tibial plateau. When there is increased pressure between the femoral and tibial surfaces in an affected compartment of the knee joint, and particularly dynamic pressure, cartilage degeneration can occur at the contact surface producing pain in the joint.

Orthopedic knee braces are commonly applied to the leg to treat osteoarthritis in the knee. Such braces typically include an upper support portion for securing to the upper leg of the wearer, a lower support portion for securing to the lower leg, and one or more hinge assemblies pivotally interconnecting the upper and lower support portions. In a two-sided knee brace, a hinge assembly is located at each side of the knee when the brace is worn. A condyle pad is typically located between each hinge assembly and side of the knee.

Knee braces of the type described serve to reduce osteoarthritis pain in the knee joint by applying a three-point load to the leg. A force is applied to the side of the knee opposite the affected compartment by causing the adjacent condyle pad to forcibly contact the side of the knee. This is typically accomplished by increasing the thickness of the adjacent condyle pad or by moving the pad closer to the knee using a jackscrew or other means. Alternatively, a force is sometimes applied opposite the affected compartment of the knee by means of an adjustable force strap which extends around the leg in a helical fashion from the upper support portion to the lower support portion. In either case, counteracting forces are applied to the leg in the medial/lateral plane above and below the knee on the side of the affected compartment by the upper and lower support portions. The resulting three-point load on the leg serves to reduce osteoarthritis pain in the knee joint by reducing the load in the affected compartment of the knee.

While such knee braces have proven effective in relieving osteoarthritis pain in the knee joint, the upper and lower support portions of such braces lack sufficient adjustability for optimal fit on various leg shapes and for various loads to relieve osteoarthritis pain. The upper and lower support portions are typically relatively rigid and are not adapted to conform to the leg shape of the wearer. As a result, such braces are often bulky, uncomfortable, and ill-fitting. In addition, when such braces are adjusted to apply a force to the knee or to fit the leg of a patient, stress is generated in the hinge assemblies of the knee braces. This stress causes wear on the components of the hinge assemblies and, in extreme cases, can result in binding of the hinge assemblies.

SUMMARY OF THE INVENTION

Accordingly, it is a principle object and advantage of the present invention to overcome some or all of these limitations and to provide an improved orthopedic knee brace and hinge assembly therefor.

In a preferred embodiment, the present invention provides an orthopedic knee brace including an upper support portion, a lower support portion, and medial and lateral hinge assemblies pivotally interconnecting the upper and lower support portions. The upper support portion includes an upper leg cuff for positioning over the front of the thigh of the wearer and medial and lateral support arms extending from the upper leg cuff to the medial and lateral hinge assemblies. The lower support portion includes a lower leg cuff for positioning over the calf of the wearer and medial and lateral support arms extending from the lower leg cuff to the medial and lateral hinge assemblies. An adjustment device is located between each leg cuff and support arm on one side of the brace.

The adjustment devices allow adjustment of the knee brace to fit a variety of different leg shapes. Once fitted, the adjustment devices allow further adjustment of the brace to apply a three-point load to the leg to relieve osteoarthritis pain in the knee. The hinge assemblies allow medial and lateral articulation of the support arms as the brace is adjusted, allowing the brace to conform to the shape of the leg of the wearer. Because the hinge assemblies allow medial and lateral articulation of the support arms, adjustment of the knee brace does not generate stress in the hinge assemblies, which can otherwise cause excessive loading and wear and tear on the hinge assemblies during repeated flexions and extentions.

Moreover, a knee brace incorporating one or more hinge assemblies having features and advantages in accordance with the invention can be made more compact and lightweight for a given amount of knee bracing. A knee brace incorporating one or more hinge assemeblies having features and advantages in accordance with the invention can also be made with both medial and lateral support arms, without compromising the desired compact size and while greatly reducing the likelihood of the knee brace to bind at one or more of the hinges when used on a leg having a varus or vulgus shape. Thus, more reliable bracing is provided.

In accordance with one embodiment the present invention provides a hinge assembly for an orthopedic knee brace having upper and lower support arms. The hinge assembly includes a hinge plate and first and second gear members pivotally connected to the hinge plate. The first gear member is coupled for rotation with the upper support arm and has an articulation surface adjacent a surface of the upper support arm. The second gear member is coupled for rotation with the lower support arm and has an articulation surface adjacent a surface of the lower support arm. The hinge assembly allows articulation of the upper and lower support arms on the articulation surfaces in a plane substantially perpendicular to a plane of rotation of the first and second gear members.

In accordance with another embodiment the present invention provides a hinge assembly for an orthopedic knee brace having upper and lower support arms. The hinge assembly includes a hinge plate and first and second gear members pivotally connected to the hinge plate. The first and second gear members have intermeshing gear teeth on adjacent perimeters thereof. The first gear member is coupled for rotation with the upper support arm and has an articulation surface adjacent a surface of the upper support arm. The second gear member is coupled for rotation with the lower support arm and has an articulation surface adjacent a surface of the lower support arm. The hinge assembly allows articulation of the upper and lower support arms on the articulation surfaces in a plane substantially perpendicular to a plane of rotation of the first and second gear members.

In accordance with another embodiment a hinge assembly is provided for an orthopedic knee brace having upper and lower support arms. The hinge assembly includes a hinge plate and first and second gear members pivotally connected to the hinge plate. The first and second gear members have mating gear teeth on adjacent portions thereof. The first gear member is coupled for rotation with the upper support arm and has an articulation surface adjacent a surface of the upper support arm. The second gear member is coupled for rotation with the lower support arm and has an articulation surface adjacent a surface of the lower support arm. The hinge assembly allows articulation of the upper and lower support arms on the articulation surfaces while maintaining coplanarity of the first and second gear members.

In accordance with another embodiment the present invention provides an orthopedic knee brace having an upper leg cuff mountable above the knee of a wearer and a lower leg cuff mountable below the knee of the wearer. Upper and lower support arms extend from the upper and lower leg cuffs to a hinge assembly disposed between the upper and lower leg cuffs. The hinge assembly comprises a hinge plate and first and second gear members pivotally connected to the hinge plate. The first and second gear members have intermeshing gear teeth on adjacent portions thereof. The first gear member is coupled for rotation with the upper support arm and has an articulation surface adjacent a surface of the upper support arm. The second gear member is coupled for rotation with the lower support arm and has an articulation surface adjacent a surface of the lower support arm. An adjustment device is coupled to at least one of the support arms for allowing adjustment of an angle or amount of torsion between the support arm and associated leg cuff. The hinge assembly allows such adjustment while maintaining relative coplanarity of the first and second gear members.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

Figure 1:
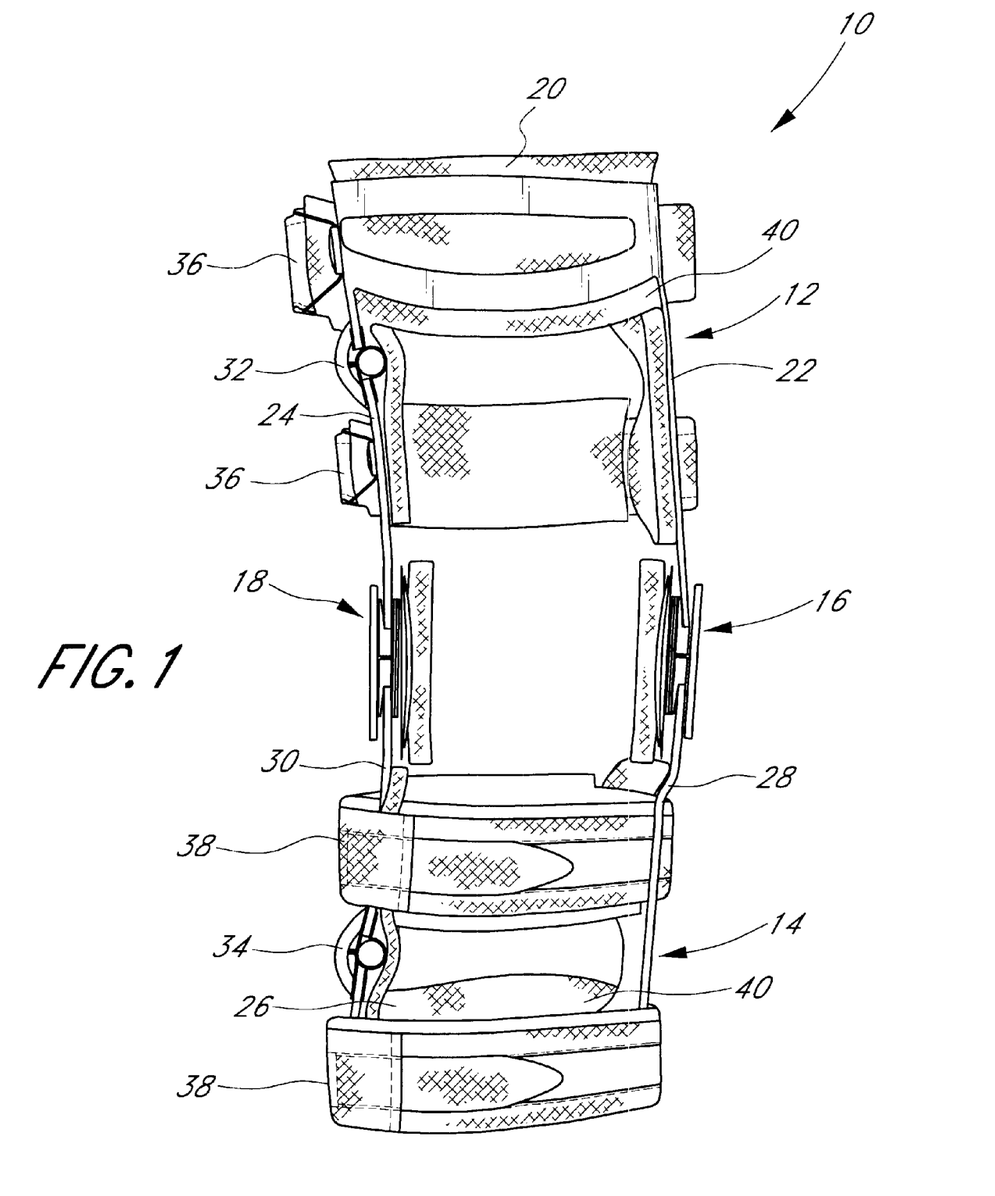
FIG. 1 is a front view of a knee brace having features in accordance with the present invention.

One embodiment of an orthopedic knee brace 10 having features and advantages in accordance with the present invention is illustrated in FIG. 1. The particular knee brace 10 illustrated is configured to be applied either to the right leg of a wearer to treat osteoarthritis in the medial compartment of the right knee, or to the left leg to treat osteoarthritis in the lateral compartment of the left knee. However, it will be apparent to those skilled in the art that the knee brace 10 can also be modified to treat osteoarthritis in the lateral compartment of the right knee or the medial compartment of the left knee. For purposes of discussion herein, it will be assumed that the brace 10 is to be applied to the right leg of the wearer to treat osteoarthritis in the medial compartment of the right knee.

Referring to FIG. 1, the knee brace 10 includes an upper support portion 12, a lower support portion 14, and medial and lateral hinge assemblies 16, 18. The upper and lower support portions 12, 14 are pivotally connected to one another via the medial and lateral hinge assemblies 16, 18. The upper support portion 12 includes an upper leg cuff 20 for positioning over the front of the thigh of the wearer (see FIG. 10) and medial and lateral support arms 22, 24 extending from the upper leg cuff 20 to the medial and lateral hinge assemblies 16, 18. The lower support portion 14 includes a lower leg cuff 26 for positioning over the calf of the wearer and medial and lateral support arms 28, 30 extending from the lower leg cuff 26 to the medial and lateral hinge assemblies 16, 18. A first adjustment device 32 is located between the upper leg cuff 20 and the upper lateral support arm 24, and a second adjustment device 34 is located between the lower leg cuff 26 and the lower lateral support arm 30.

The upper support portion 12 is secured to the upper leg of the wearer with adjustable straps 36 which extend around the back of the upper leg. The lower support portion 14 is secured to the lower leg by adjustable straps 38 which extend around the front and back of the lower leg. For ease of adjustment, the straps 36, 38 are preferably fastened with a hook and pile fastener such as VELCRO™.

The upper and lower support portions 12, 14 are preferably made of aluminum, but can be made from any lightweight, high-strength metal, plastic, or composite material. The interior surface of each of the upper and lower support portions 12, 14 is covered with padding 40 to provide a comfortable fit against the leg of the wearer. The padding 40 is preferably made from a resilient foam material. However, inflated bladders, gels or other types of padding may also be used.

Figure 2:
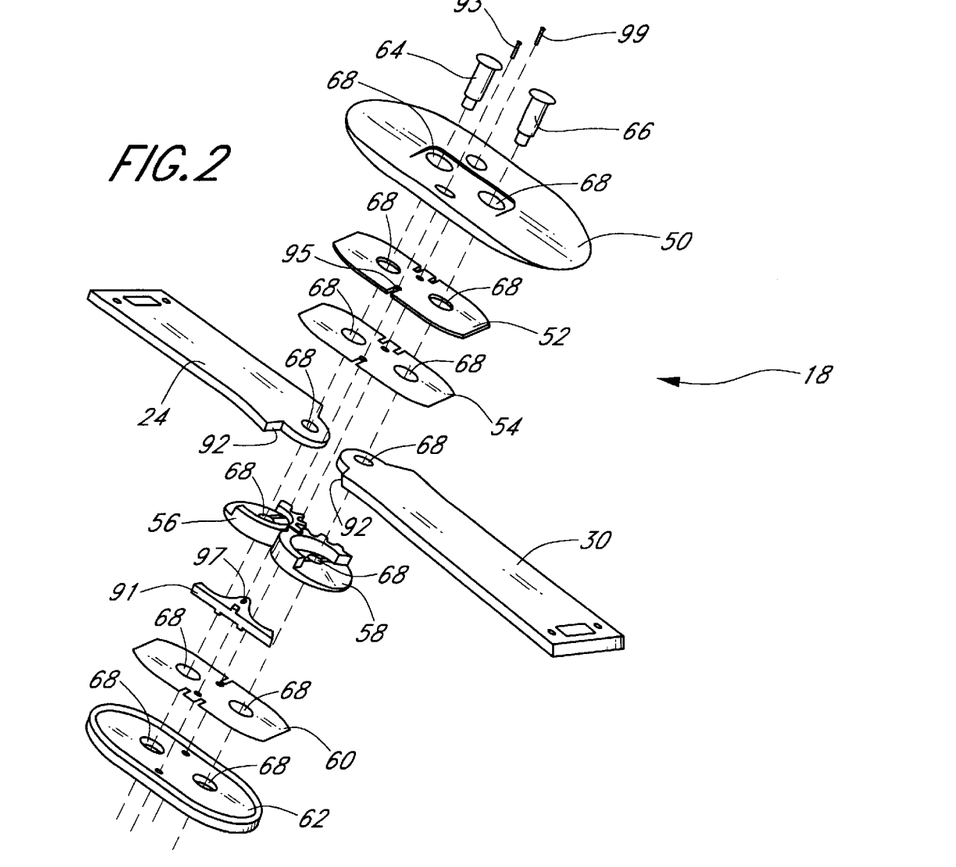
FIG. 2 is an exploded perspective view of the lateral hinge assembly of the knee brace of FIG. 1.

FIG. 2 is an exploded perspective view of the lateral hinge assembly 18 of the knee brace 10. On a side of the lateral support arms 24, 30 adjacent the knee, the hinge assembly 18 comprises a condyle pad holder 50, an inner hinge plate 52, and an inner bearing plate 54. On a side of the support arms 24, 30 opposite the knee, the hinge assembly 18 comprises a first gear member 56, a second gear member 58, an outer bearing plate 60, and an outer hinge plate 62. First and second hinge pins 64, 66 extend from the condyle pad holder 50 to the outer hinge plate 62 through openings 68 provided in the support arms 24, 30 and each of the components of the hinge assembly 18. The hinge pins 64, 66 are attached to the outer hinge plate 62, preferably by swaging the ends thereof, and serve to fasten the hinge assembly 18 together and provide pivotal securement of the arms 24, 30.

Figure 3:
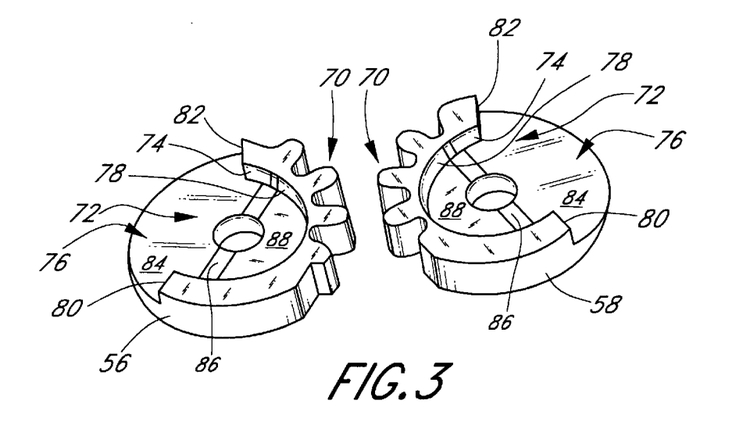
FIG. 3 is a perspective view of the gear members of the lateral hinge assembly of FIG. 2.

FIG. 3 is a perspective view of the first and second gear members 56, 58 of the lateral hinge assembly 18. In the illustrated embodiment, the first and second gear members 56, 58 are generally cylindrical in shape and have a number of involute gear teeth 70 on adjacent perimeters thereof. Each of the first and second gear members 56, 58 includes a generally recessed area 72. The recessed area 72 is defined by a wall surface 74 and a base surface 76. The wall surface 74 includes a curvilinear portion 78, an anterior bearing surface 80, and a posterior bearing surface 82. The base surface 76 includes an inclined portion 84, a plateau 86, and a declined portion 88, together defining an articulating surface.

Figure 4:
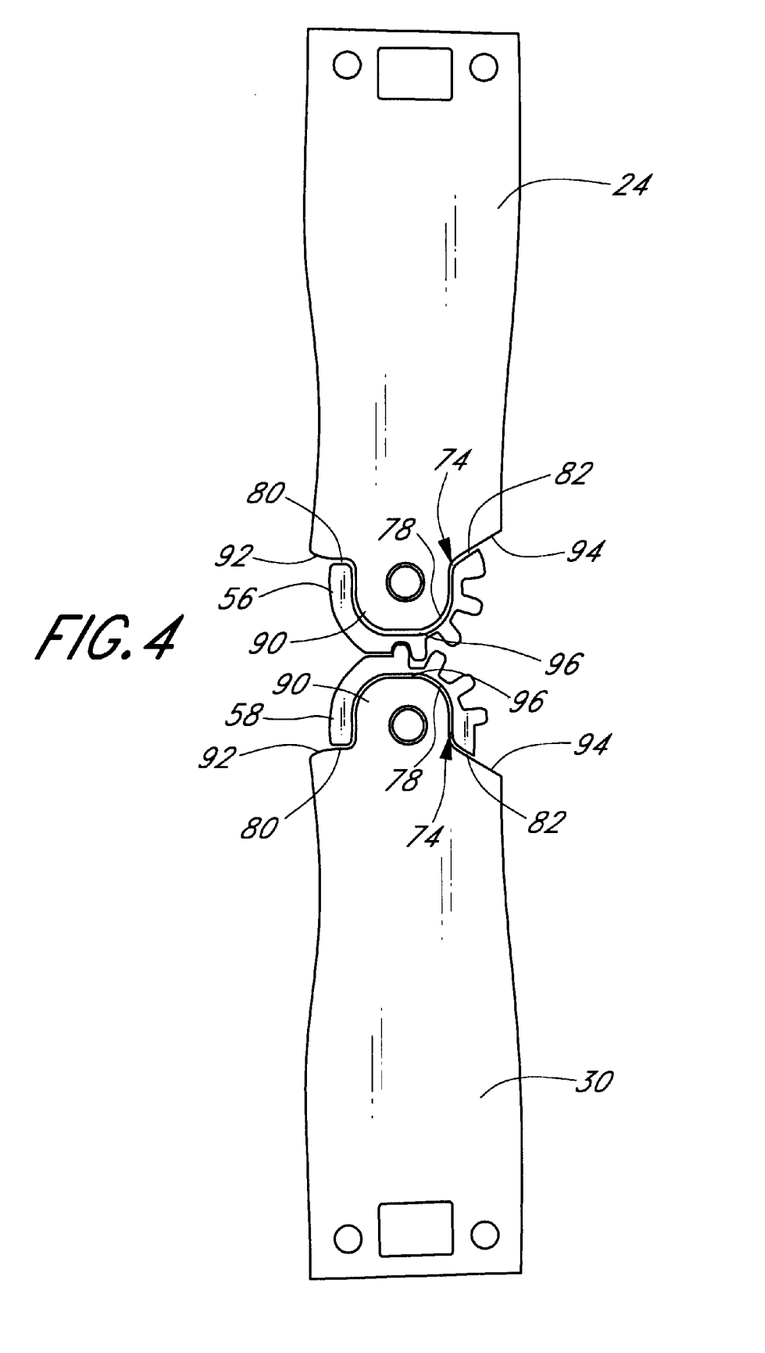
FIG. 4 is a left side view of the upper and lower lateral support arms and first and second gear members of the knee brace of FIG. 1.

Referring to FIG. 4, each of the support arms 24, 30 has a tab 90 at an end thereof and anterior and posterior shoulders 92, 94 on either side of the tab 90. The tab 90 of the upper support arm 24 has a shape that generally corresponds with the shape of the curvilinear portion 78 of the wall surface 74 of the first gear member 56. The tab 90 of the lower support arm 30 has a shape that generally corresponds with the shape of the curvilinear portion 78 of the wall surface 74 of the second gear member 58. The ends of the upper and lower support arms 24, 30 fit within the recessed areas 72 of the first and second gear members 56, 58 as shown. The anterior and posterior shoulders 92, 94 of the support arms 24, 30 abut the anterior and posterior bearing surfaces 80, 82 of the gear members 56, 58, preferably with a slight gap 96 being formed between each tab 90 and the curvilinear portion 78 of the wall surface 74 to allow medial/lateral rocking or articulation of the support arms 24, 30.

Figure 5A:
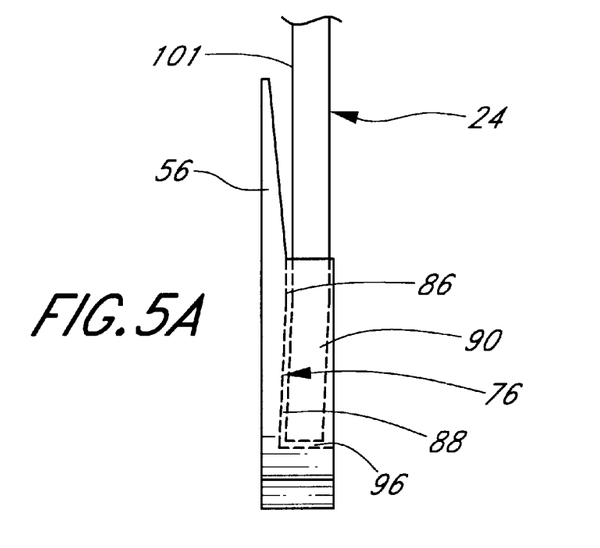
FIG. 5A is a front view of the of the upper lateral support arm and first gear member of the knee brace of FIG. 1, with the upper lateral support arm at a first position relative to the first gear member.

FIG. 5A is a front view of the first gear member 56 and the upper support arm 24 with the upper support arm 24 at a first extreme position. An outer surface 101 of the support arm 24 rests against the base surface 76 of the gear member 56. In the first extreme position, the tab 90 of the support arm 24 rests against the plateau 86 and the declined portion 88 of the base surface 76. Preferably, tab 90 is bent slightly toward the base surface 76 of the gear member 56 to roughly parallel the declined portion 88.

Figure 6:
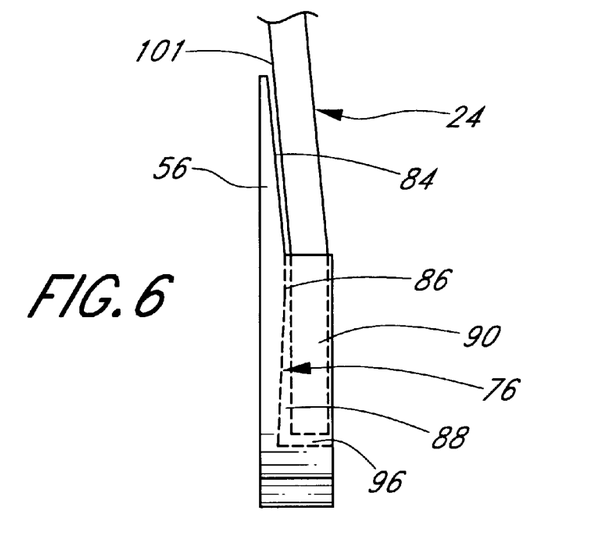
FIG. 6 is a front view of the upper lateral support arm and first gear member of the knee brace of FIG. 1, with the upper lateral support arm at a second position relative to the first gear member.

FIG. 6 is a front view of the first gear member 56 and the upper support arm 24 with the upper support arm 24 at a second extreme position. In the second extreme position, the outer surface of the support arm 24 rests against the inclined portion 84 and the plateau 86 of the base surface 76. The tab 90 of the support arm 24 does not contact the declined 88 portion of the base surface 76. Because the tab 90 is bent slightly toward base surface 76, the end of the tab 90 does not extend out of the recessed area 72 and thus will not tend to pry the hinge assembly 18 apart when fully assembled.

Those skilled in the art will appreciate that the upper support arm 24 articulates on the base surface 76 of the first gear member 56 between the first and second extreme positions. The anterior and posterior shoulders 92, 94 of the upper support arm 24 pivot on the anterior and posterior bearing surfaces 82 of the wall surface 74. Because of the small gap 96 between the end of the tab 90 and the curvilinear portion 78 of the wall surface 74, the end of the tab 90 advantageously does not interfere with the curvilinear portion 78 of the wall surface 74 as the upper support arm 24 articulates between the first and second positions. The lower support arm 30 articulates on the base surface 76 of the second gear member 58 in a manner similar to that of the upper support arm 24 and first gear member 56.

The particular illustrated configuration of the gear members 56, 58 and support arms 24, 30 described above is merely a preferred embodiment thereof. It is to be understood that the gear members 56, 58 and support arms 24, 30 can alternatively be constructed and configured in a wide variety of other ways giving due consideration to the goals of providing a hinged connection between the upper and lower arms of the brace while facilitating a predetermined amount of medial and lateral articulation of the arms relative to the hinge/gear assembly.

Figure 5B:
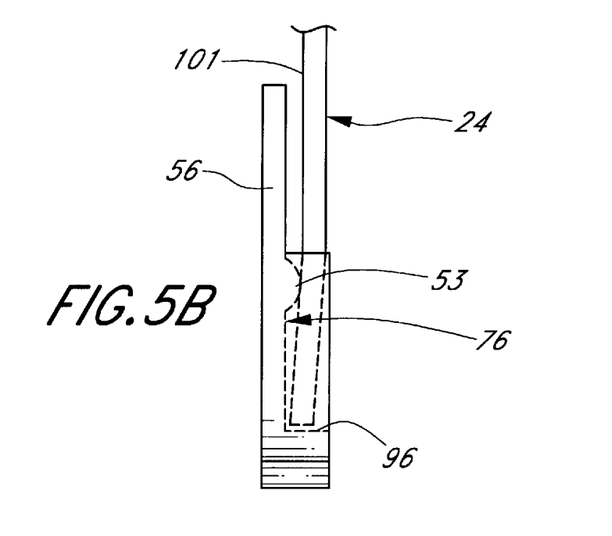
FIG. 5B is a front view of a first alternative embodiment of the upper lateral support arm and first gear member of the knee brace of FIG. 1, with the upper lateral support arm at a first position relative to the first gear member.
Figure 5C:
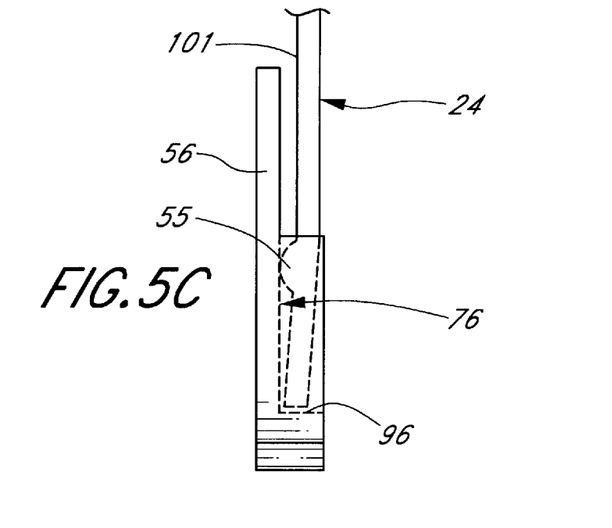
FIG. 5C is a front view of a second alternative embodiment of the upper lateral support arm and first gear member of the knee brace of FIG. 1, with the upper lateral support arm at a first position relative to the first gear member.

FIG. 5B illustrates an alternative embodiment of the first gear member 56 and upper support arm 24 in the first extreme position of FIG. 5A. In this alternative embodiment, the base surface 76 of the first gear member 56 is generally planar, with the exception of a raised bump 53 provided thereon. The support arm 24 articulates on the bump between the first and second extreme positions. FIG. 5C illustrates a second alternative embodiment of the first gear member 56 and upper support arm 24, wherein the base surface 76 of the first gear member 56 is planar, and a bump 55 is provided on the support arm 24. Those skilled in the art will readily appreciate that suitable articulating surfaces may be provided on either the support arm, the gear member, or both, as desired.

Figure 7:
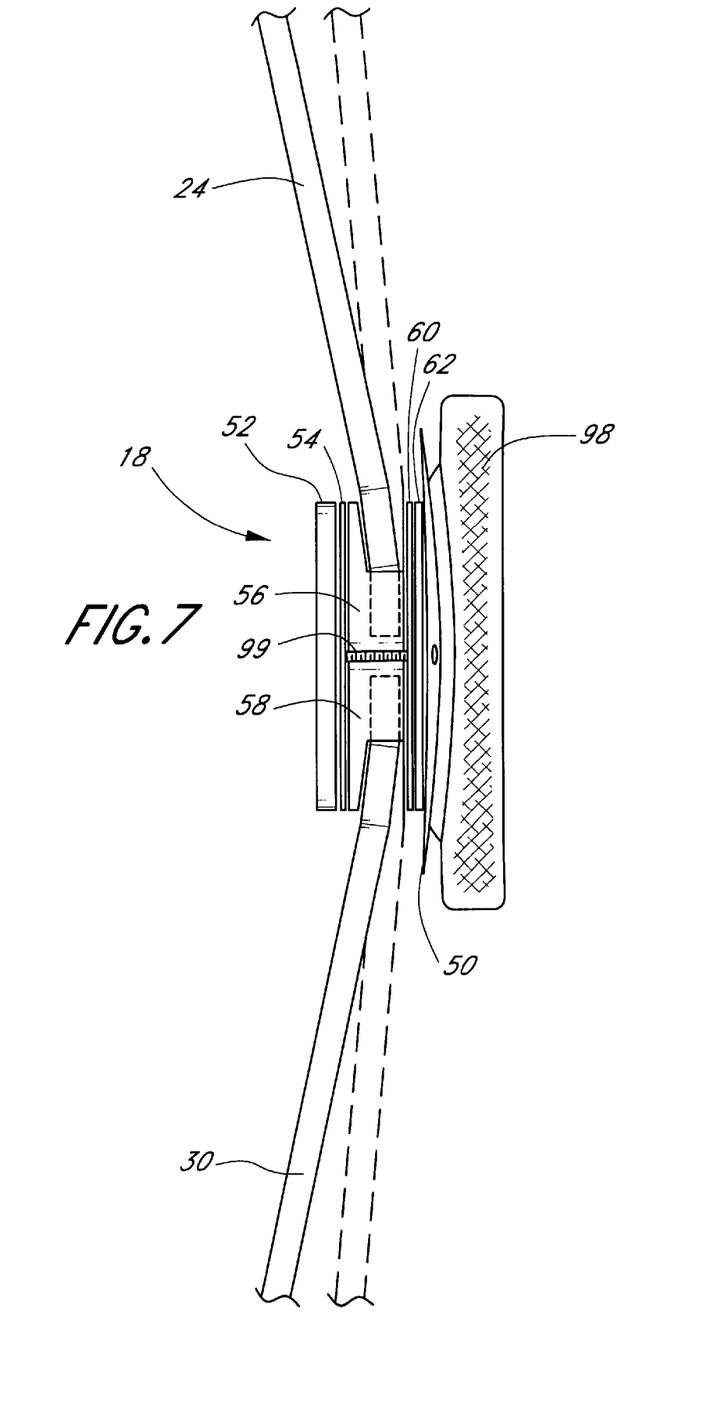
FIG. 7 is a front view of the lateral hinge assembly and upper and lower lateral support arms of the knee brace of FIG. 1.

FIG. 7 is a front view of the lateral hinge assembly 18 and the upper and lower lateral support arms 24, 30 of the knee brace 10. The first and second gear members 56, 58 are sandwiched between the inner and outer bearing plates 54, 60 and hinge plates 52, 62. The bearing plates 54, 60 are preferably fabricated from a durable, low-friction plastic such as ABS, nylon, DELRIN™, or TEFLON™ to provide a low-friction interface between the gear members 56, 58 and bearing plates 54, 60. A condyle pad 98 is removably attached to the condyle pad holder 50 with a hook and pile or other type of fastener. The condyle pad 98 is preferably made from a resilient foam or other cushioning material. However, an inflatable bladder can also be used.

The first gear member 56 rotates about the first hinge pin 64 (not shown) with the upper lateral support arm 24 engaged therewith. The second gear member 58 rotates about the second hinge pin 66 (not shown) with the lower lateral support arm 30 engaged therewith. The gear teeth 70 of the first and second gear members 56, 58 mesh to provide a controlled rotation of the gear members 56, 58 and the upper and lower support arms 24, 30. The upper and lower support arms 24, 30 are allowed to articulate between the first and second positions on the base surfaces 72 of the first and second gear members 56, 58 in a plane perpendicular to the plane of rotation.

If desired, flexion and/or extension stops can be provided in the hinge assembly 18 to limit the flexion and/or extension of the leg. An extension stop 91 is shown in FIG. 2 located anterior to the first and second gear members 56, 58. The extension stop 91 is fastened to the hinge assembly 18 by a threaded fastener 93 which engages a threaded hole 95 in the inner hinge plate 52 and extends through a hole 97 in the extension stop 91. When the desired extension limit is reached, the anterior shoulders 92 of the upper and lower support arms 24, 30 abut the ends of the extension stop 91 to prevent further rotation of the support arms 24, 30. Similarly, a flexion stop (not shown) can be located posterior to the first and second gear members 56, 58 and fastened to the hinge assembly 18 by a second threaded fastener 99 if desired to limit flexion of the leg. Alternatively, or in addition to the flexion and extension stops 91, the gear members 56, 58 themselves can be configured to limit flexion and extension by providing interfering portions on the perimeters thereof. A wide variety of other suitable structures may also be used as will be readily apparent to these skilled in the art.

Figure 8:
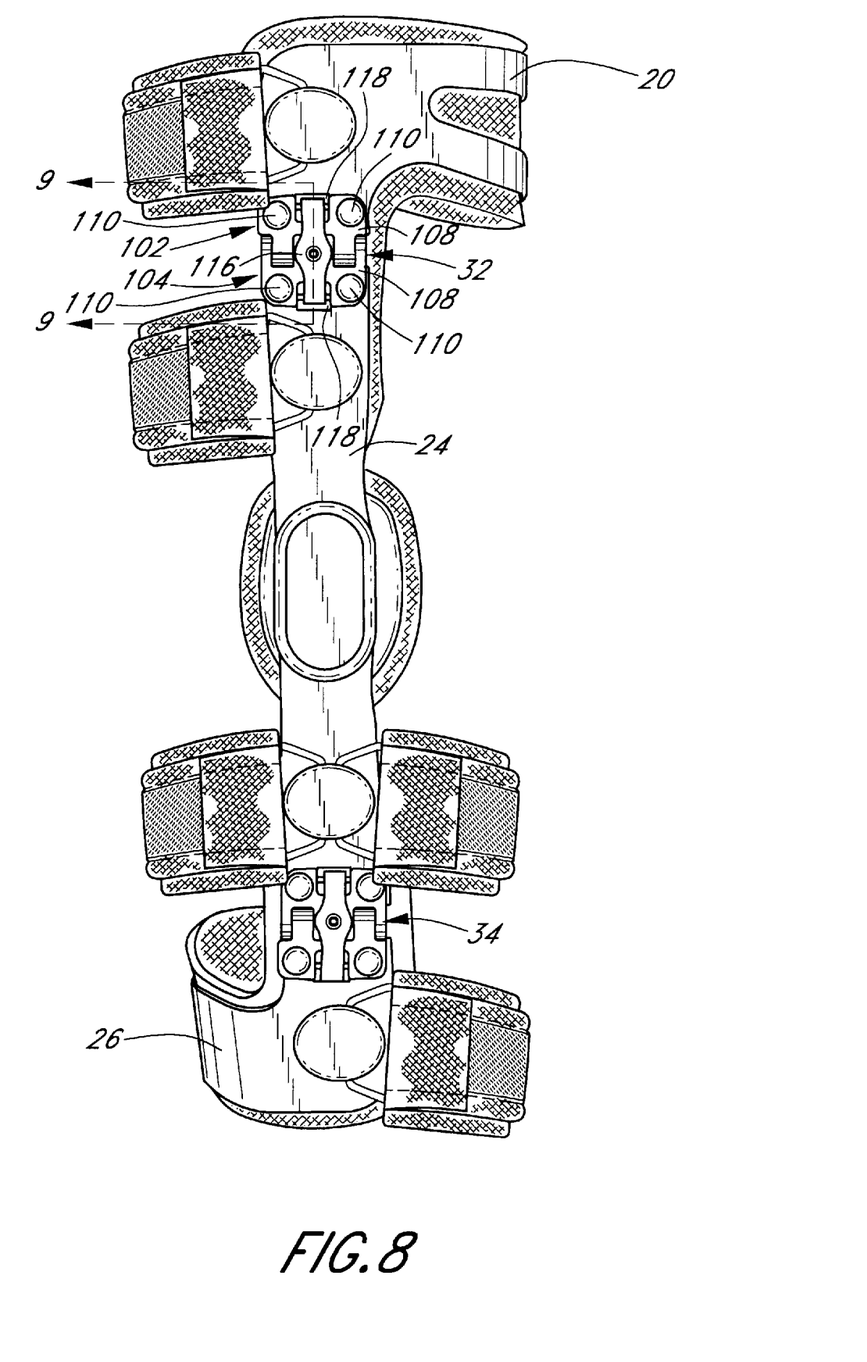
FIG. 8 is a right side view of the knee brace of FIG. 1.

FIG. 8 is a lateral side view of the knee brace 10 showing the first and second adjustment devices 32, 34. In a preferred embodiment, the adjustment devices 32, 34 are of a type described in U.S. Pat. No. 5,766,140 assigned to the assignee of the present invention and hereby incorporated by reference herein.

Figure 9:
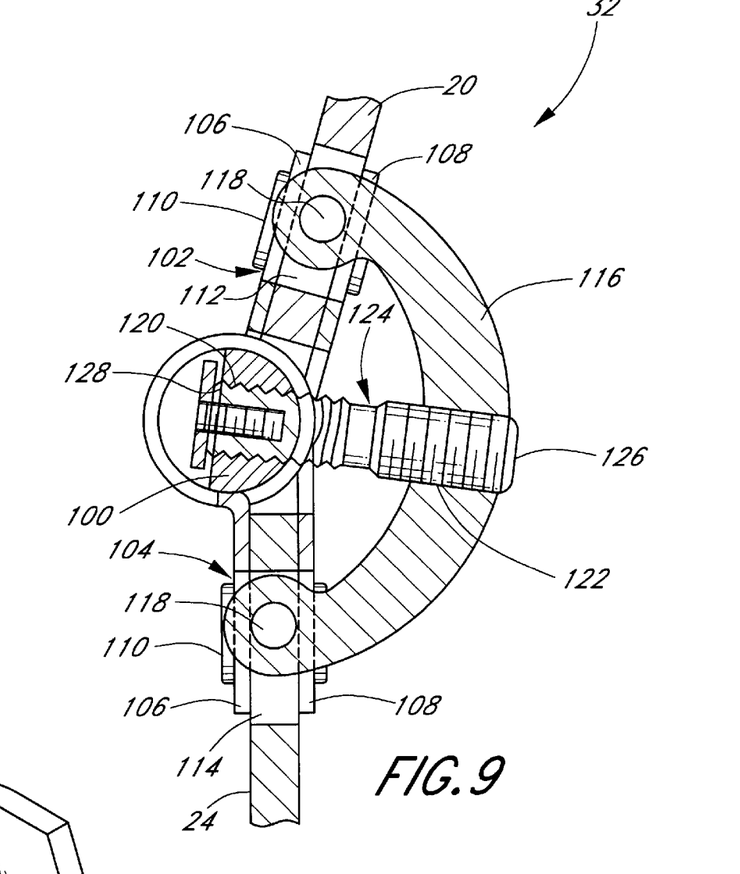
FIG. 9 is a cross-sectional view of the upper adjustment device of the knee brace of FIG. 1, taken along the line 9—9 in FIG. 8.

FIG. 9 is a cross-sectional view of the first adjustment 32 device taken along the line 9—9 in FIG. 8. Referring to FIGS. 8 and 9, the first adjustment device 32 comprises a hinge pin 100 having first and second hinge portions 102, 104 rotatably mounted thereon. Each of the first and second hinge portions 102, 104 includes an inner member 106 and an outer member 108. The first hinge portion 102 is fastened to the upper leg cuff 20 by rivets 110 which extend from the outer member 108 to the inner member 106 of the first hinge portion 102 through openings formed in the upper leg cuff 20. The second hinge portion 104 is fastened to the upper support arm 24 by rivets 110 which extend from the outer member 108 to the inner member 106 of the second hinge portion 104 through openings formed in the upper support arm 24.

A rectangular opening 112 is provided in the upper leg cuff 20 between the inner and outer members 106, 108 of the first hinge portion 102. A second rectangular opening 114 is provided in the upper support arm 24 between the inner and outer members 106, 108 of the second hinge portion 104. An arch bar 116 extends from the rectangular opening 112 in the upper leg cuff 20 to the rectangular opening 114 in the upper support arm 24. Each end of the arch bar 116 has a guide pin 118 extending therethrough. The guide pins 118 are movably confined in the rectangular openings 112, 114 by the inner and outer members 106, 108 of the first and second hinge portions 102, 104.

The hinge pin 100 has a right-hand threaded hole 120 extending through its axial midpoint. The arch bar 116 has a left-hand threaded hole 122 located over the right-hand threaded hole 120 in the hinge pin 100. A single adjustment screw 124 having a left-hand threaded end 126 and a right-hand threaded end 128 engages both the left-hand threads of the arch bar 116 and the right-hand threads of the hinge pin 100.

The left-hand threaded end 126 of the adjustment screw 124 is adapted to receive a tool such as a screwdriver or Allen-type wrench for turning the adjustment screw 124. When the adjustment screw 124 is turned counterclockwise, the hinge pin 100 is moved away from the arch bar 116. The guide pins 118 at the ends of the arch bar 116 pull against the outer members 108 of the first and second hinge portions 102, 104 causing the first and second hinge portions 102, 104 to rotate about the hinge pin 100. When the adjustment screw 124 is turned clockwise, the hinge pin 100 is moved toward the arch bar 116 and the guide pins 118 push against the inner members 106 of the first and second hinge portions 102, 104. Thus, by adjusting the distance between the arch bar 116 and the hinge pin 100, the angle between the first and second hinge portions 102, 104 is affected. Because the first hinge portion 102 is fastened to the upper leg cuff 20 and the second hinge portion 104 is fastened to the upper support arm 24, the angle between the upper leg cuff 20 and the upper support arm 24 can be adjusted by turning the adjustment screw 124.

The second adjustment device 34 is identical to the first 32 except that the hinge portions 102, 104 of the second adjustment device 34 are coupled to the lower leg cuff 26 and the lower lateral support arm 30. Thus, the angle between the lower leg cuff 26 and the lower support arm 30 can also be adjusted by turning the adjustment screw 124 of the second adjustment device 34.

Figure 10:
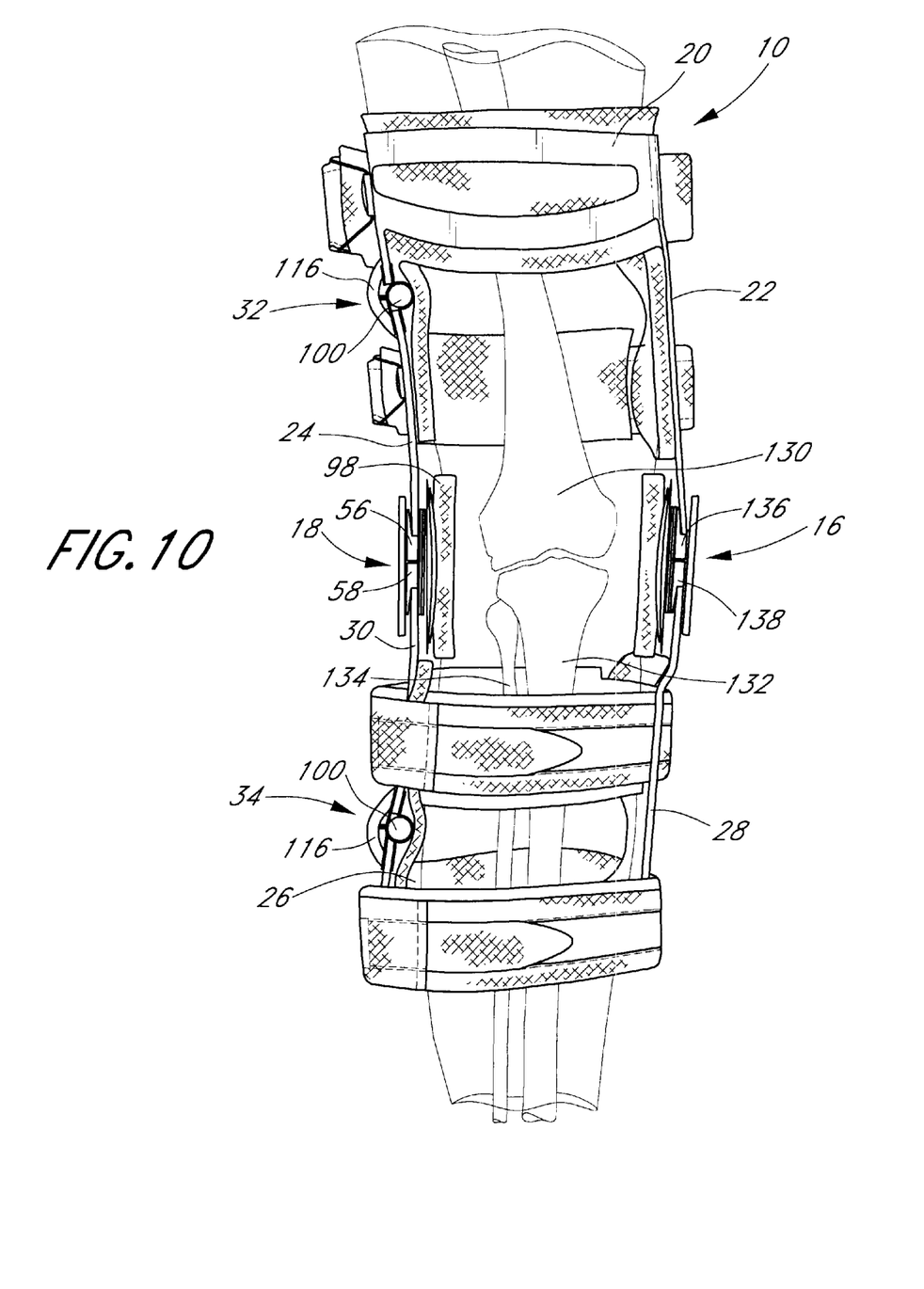
FIG. 10 is a front view of the knee brace of FIG. 1 applied to the right leg of a wearer.

FIG. 10 is a front view of the knee brace 10 applied to the right leg of a wearer. The femur 130, tibia 132, and fibula 134 of the right leg are shown. To treat osteoarthritis in the medial compartment of the right knee, the brace 10 is fitted to the right leg with the support arms 24, 30 and adjustment devices 32, 34 located on the lateral side of the leg. The medial support arms 22, 28 can be bent or otherwise shaped, as desired or necessary, to comfortably fit the shape of the wearer's leg. A force is then applied to the opposite (lateral) side of the knee by turning the adjustment screws 124 of the first and second adjustment devices 32, 34 clockwise. The hinge pins 100 of the adjustment devices 32, 34 are thereby drawn toward the arch bars 116 causing the upper and lower support arms 24, 30 to rotate toward the leg relative to the upper and lower leg cuffs 20, 26.

The lateral hinge assembly 18 is moved toward the knee by the rotation of the upper and lower support arms 24, 30. As the hinge assembly 18 moves toward the knee, the ends of the upper and lower support arms 24, 30 articulate on the base surfaces 76 of the first and second gear members 56, 58. The lateral hinge assembly 18 applies a force to the lateral side of the knee via the condyle pad 98. Counteracting forces are applied above and below the knee on the medial side of the leg by the upper and lower leg cuffs 20, 26. The resulting three-point load on the leg serves to reduce the load in medial compartment of the knee.

By adjusting the first and second adjustment devices 32, 34, the knee brace 10 can be fitted to a varus (bowlegged) or valgus (knock-kneed) leg. Once fitted, the adjustment devices 32, 34 can be further adjusted to apply a corrective load to the leg. The medial and lateral adjustability of the support arms 24, 30 allows the brace 10 to accommodate a wide variety of leg shapes and sizes.

Because the upper and lower support arms 24, 30 are allowed to articulate on the base surfaces 76 of the first and second gear members 56, 58 (FIG. 7), adjustment of the adjustment devices 32, 34 does not generate stress in the hinge assembly 18. The first gear member 56 is maintained in substantially the same plane as the second gear member 58 regardless of the angle of the support arms 24, 30 relative to the leg cuffs 20, 26. Because coplanarity of the first and second gear members 56, 58 is maintained, binding of the hinge assembly 18 is prevented even when the angle between the support arms 24, 30 and leg cuffs 20, 26 is relatively great. Wear on the gear teeth 70 of the first and second gear members 56, 58 is thus minimized.

In a preferred embodiment, the medial hinge assembly 16 is the mirror image of the lateral hinge assembly 18 except that the gear members 136, 138 of the medial hinge assembly 16 are located on a side of the medial support arms 22, 28 adjacent the knee. The upper and lower medial support arms 22, 28 articulate on the gear members 136, 138 of the medial hinge assembly 16 in a manner similar to that of the lateral support arms 24, 30 and gear members 56, 58 of the lateral hinge assembly 18. As the adjustment devices 32, 34 are adjusted to increase the treatment force applied to the lateral side of the knee, the medial support arms 22, 28 can be bent or otherwise allowed to articulate on the gear members 136, 138 of the medial hinge assembly 16 away from the side of the knee. As a result, the force applied by the medial hinge assembly 16 on the medial side of the knee is relatively small and thus has little effect in counteracting the treatment force applied to the lateral side of the knee.

In the illustrated embodiment, the gear members 56, 58 of the lateral hinge assembly 18 are located on a side of the lateral support arms 24, 30 opposite the knee. However, it will be apparent to those skilled in the art that the gear members 56, 58 of the lateral hinge assembly 18 can alternatively be located on a side of the support arms 24, 30 adjacent the knee. When the brace 10 is so configured, the support arms 24, 30 articulate from the second extreme position (wherein the support arms 24, 30 contact the inclined surfaces 84 and plateaus 86 of the first and second gear members 56, 58) to the first extreme position (wherein the support arms 24, 30 contact the plateaus 86 and declined surfaces 88 of the first and second gear members 56, 58) as the lateral hinge assembly 18 moves toward the medial hinge assembly 16. Similarly, it will be apparent that, while the gear members 136, 138 of the medial hinge assembly 16 are located on a side of the medial support arms 22, 28 adjacent the knee in the illustrated embodiment, the gear members 136, 138 can alternatively be located on a side of the support arms 22, 28 opposite the knee. Thus, in an alternative embodiment, the medial and lateral hinge assemblies 16, 18 may be mirror images of one another. Advantageously, this would allow the same hinge assembly configuration to be used for both the medial and lateral sides.

Figure 11:
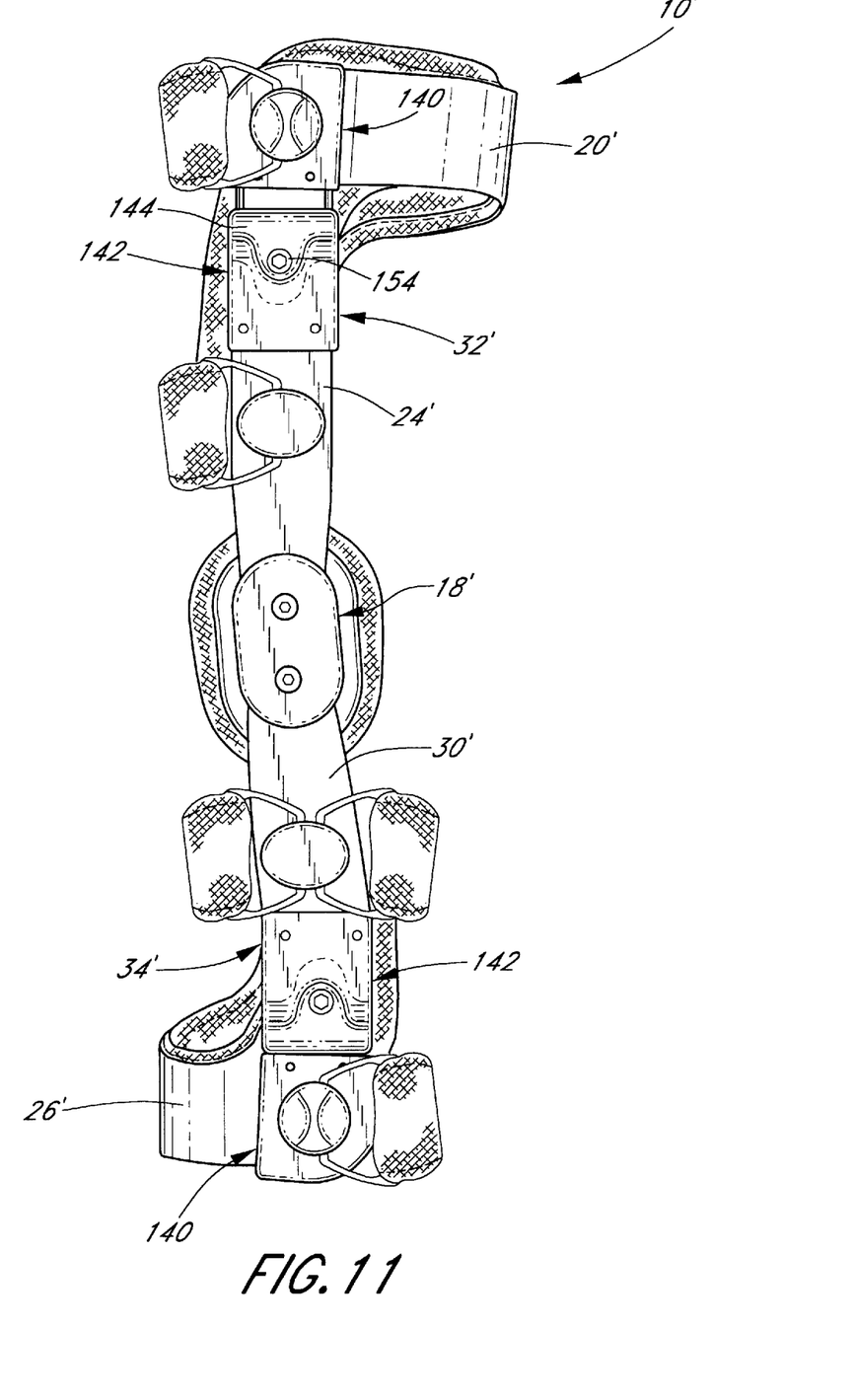
FIG. 11 is a right side view of an alternative preferred embodiment of a knee brace having features in accordance with the present invention.

FIG. 11 is a lateral side view of an alternative preferred embodiment of the knee brace 10' having first and second adjustment devices 32', 34'. In this embodiment, the first adjustment device 32' comprises a first part 140 coupled to the upper leg cuff 20' and a second part 142 coupled to the upper lateral support arm 24'. The second part 142 of the adjustment device 32' includes a hollow casing 144 having anterior and posterior side walls 146, 148, as shown in FIG. 12.

Figure 12:
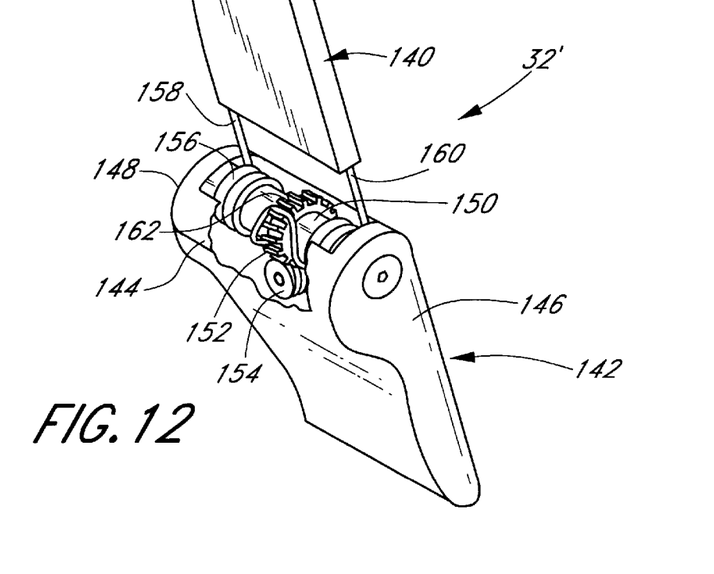
FIG. 12 is a perspective view of the upper adjustment device of the knee brace of FIG. 11.

A portion of the hollow casing 144 has been cut away in FIG. 12 to show the interior components of the adjustment device 32'. A shaft 150 extends across the hollow casing 144 and is rotatably mounted at its ends to the anterior and posterior side walls 146, 148 of the hollow casing 144. A driven gear 152 is fixedly mounted on the shaft 150 for rotation therewith. A worm gear 154 is rotatably mounted in the casing 144 perpendicular to the shaft 150 and mates with the driven gear 152 to turn the driven gear 152 and shaft 150. A torsion spring 156 is coiled around the shaft 150 and has first and second ends 158, 160 attached to the first part 140 of the adjustment device 32'. The driven gear 152 engages a center portion 162 of the torsion spring 156.

The worm gear 154 is adapted to receive a screwdriver or Allen-type wrench for turning the worm gear 154 in the casing 144. The worm gear 154 drives the driven gear 152 which, depending on the direction of rotation, coils or uncoils the torsion spring 156. The coils of the torsion spring 156 and the shaft 150 extending therethrough provide a spring-loaded hinge about which the first and second parts 140, 142 of the adjustment device 32' can rotate. When the torsion spring 156 is coiled by turning the worm gear 154 in a first direction, the upper lateral support arm 24' is biased toward the leg of the wearer, thereby increasing the amount of pressure applied to the knee. When the torsion spring 156 is uncoiled by turning the worm gear 154 in an opposite direction, the bias of the upper lateral support arm 24' is reduced and the amount of pressure applied to the knee is decreased. The amount of bias can therefore be adjusted by turning the worm gear 154. The second adjustment device 34' is identical to the first 32' except that the first part 140 of the adjustment device 34' is coupled to the lower leg cuff 26' and the second part 142 is coupled to the lower lateral support arm 30'.

One advantage of the adjustment devices 32', 34' of the knee brace 10' of the present embodiment is that they allow a more constant treatment force to be applied to the knee throughout the range of flexion and extension of the leg. In the normal leg, the tibia swings slightly relative to the femur in the medial/lateral plane as the leg moves between flexion and extension. In the knee brace 10 of the previous embodiment, the angle of the upper and lower lateral support arms 24, 30 is more-or-less fixed relative to the upper and lower leg cuffs 20, 26 once adjusted by the adjustment devices 32, 34. The support arms 24, 30 may flex somewhat, however, depending upon the type material from which they are made.

Because the upper and lower leg cuffs 20, 26 are secured to the upper and lower parts of the leg, the treatment force applied to the lateral side of the knee is affected by the medial and lateral movement of the tibia relative to the femur. Specifically, the treatment force applied to the lateral side of the knee via the lateral support arms 24, 30 and hinge assembly 18 is increased as the tibia moves medially relative to the femur, and decreased as the tibia moves laterally relative to the femur.

Figure 13:
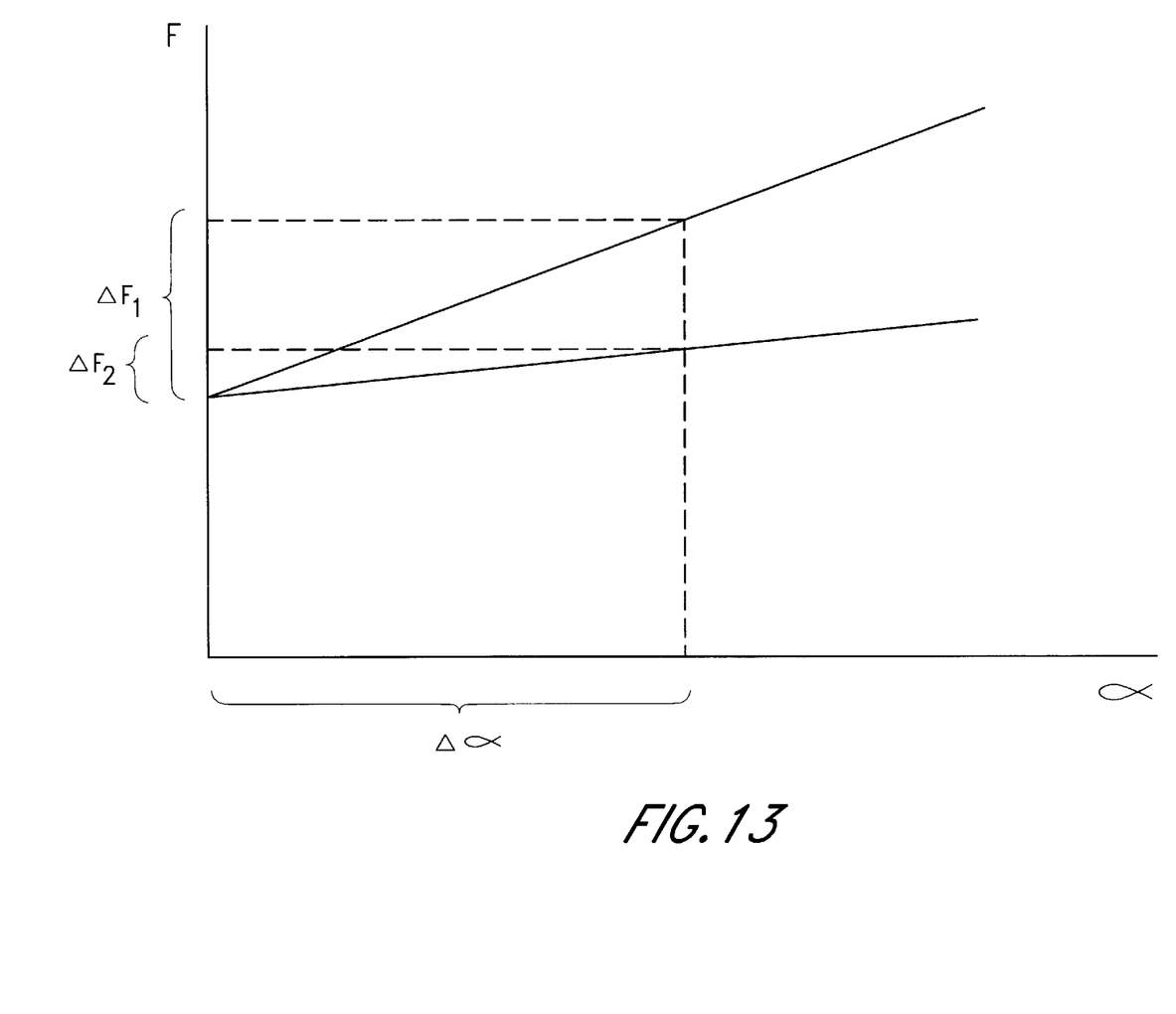
FIG. 13 is a graph showing the effect of medial and lateral movement of the tibia relative to the femur on the treatment forces applied by the braces of FIG. 1 and FIG. 11.

FIG. 13 is a graph showing the effect of the medial and lateral movement of the tibia relative to the femur on the treatment force applied to the knee. Assume that the angle between the tibia and femur of a given patient in the medial/lateral plane varies over a range Δα, typically about 7 degrees, as the patient's leg moves between flexion and extension. Because the angle of the lateral support arms 24, 30 is more-or-less fixed (subject to stiffness of the material) in the medial lateral plane relative to the upper and lower leg cuffs 20, 26, the treatment force in the medial/lateral plane applied to the lateral side of the knee via the lateral support arms 24, 30 and hinge assembly 18 varies by an amount $\Delta F_1$ from flexion to extension.

In the modified knee brace 10' of FIG. 11, the angle between the upper and lower lateral support arms 24', 30' and the upper and lower leg cuffs 20', 26' is not determined by the adjustment devices 32', 34'. The torsion springs 156 of the adjustment devices 32', 34' bias the lateral support arms 24', 30' toward the leg of the wearer, but the lateral support arms 24', 30' are not rigidly connected to the leg cuffs 20', 26'. Thus, the treatment force applied to the lateral side of the knee via the lateral support arms 24', 30' and hinge assembly 18' is generated in the torsion springs 156.

The torsion springs 156 are coiled and uncoiled slightly as the angle of the tibia relative to the femur changes during flexion and extension of the leg, allowing the support arms 24', 30' to effectively follow the motion of the leg. Preferably, the torsion springs 156 are selected and/or pre-loaded so that this slight coiling and uncoiling does not vary greatly the amount of force generated in the torsion springs 156. As a result, the amount of force applied to the lateral side of the knee is varied only by an amount $\Delta\alpha_2$ as the angle between the tibia and femur of the patient varies over the range Δα. Thus, the knee brace 10' of the present embodiment allows an even more constant treatment force to be applied to the knee throughout the range of flexion and extension of the leg. For this reason, the knee brace 10' of FIG. 11 may be preferable for some patients.

By way of example, both of the knee braces 10, 10' described herein have been adapted to treat osteoarthritis in the medial compartment of the right knee joint. However, it should be evident that both braces 10, 10' are readily adaptable for treatment of osteoarthritis in either compartment of either knee joint by obvious modifications thereof. It should also be evident that the hinge assembly described herein would be operable in other knee brace configurations, including, for example, a one-sided knee brace having a hinge assembly and support arms on only one side of the leg. Similarly, it should be evident that the hinge assembly described herein would also be operable in other type braces, such as neck, back, elbow, wrist, ankle and the like.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A hinge assembly for an orthopedic knee brace having upper and lower support arms, said binge assembly comprising:
   a hinge plate or housing;
   a first gear member pivotally connected to said hinge plate or housing and having gear teeth on a perimeter thereof, said first gear member coupled for rotation with said upper support arm and having an articulation surface adapted to rockidly engage an adjacent surface of said upper support arm; and
   a second gear member pivotally connected to said hinge plate or housing and having gear teeth intermeshing with said gear teeth of said first gear member, said second gear member coupled for rotation with said lower support arm and having an articulation surface adapted to rockingly engage an adjacent surface of said lower support arm,
   whereby said hinge assembly is configured to allow articulation of said upper and lower support arms on said articulation surfaces in a plane substantially perpendicular to a plane of rotation of said first and second gear members.

2. The hinge assembly of claim 1, wherein said first gear member has a first recessed area for receiving an end of said upper support arm, said first recessed area having a shape generally corresponding with a shape of the end of said upper support arm, and said second gear member has a second recessed area for receiving an end of said lower support arm, said second recessed area having a shape generally corresponding with a shape of the end of said lower support arm.

3. The hinge assembly of claim 2, wherein said first and second recessed areas are at least partially defined by said articulation surfaces.

4. An orthopedic knee brace incorporating the hinge assembly of claim 1, said knee brace comprising an upper leg cuff coupled to said upper support arm, a lower leg cuff coupled to said lower support arm, and an adjustment device coupled to at least one of said upper or lower support arms for allowing adjustment of an angle between said support arm and associated leg cuff.

5. A hinge assembly for an orthopedic knee brace having upper and lower support arms, said hinge assembly comprising:
   a hinge support member;
   a first gear member pivotally supported relative to said hinge support member and having gear teeth on a portion thereof, said first gear member coupled for rotation with said upper support arm and having an articulation surface adjacent a surface of said upper support arm; and
   a second gear member pivotally supported relative to said hinge support member and having gear teeth mating with said gear teeth of said first gear member, said second gear member coupled for rotation with said lower support arm and having an articulation surface adjacent a surface of said lower support arm;
   said articulation surfaces of said first and second gear members being configured to allow a predetermined degree of medial/lateral articulation of said upper and lower support arms while maintaining relative coplanarity of said first and second gear members.

6. The hinge assembly of claim 5, wherein said first gear member has a first recessed area for receiving an end of said upper support arm, said first recessed area having a shape generally corresponding with a shape of an end of said upper support arm, and said second gear member has a second recessed area for receiving an end of said lower support arm, said second recessed area having a shape generally corresponding with a shape of an end of said lower support arm.

7. The hinge assembly of claim 6, wherein said first and second recessed areas are at least partially defined by said articulation surfaces.

8. An orthopedic knee brace incorporating the hinge assembly of claim 5, said knee brace comprising an upper leg cuff coupled to said upper support arm, a lower leg cuff coupled to said lower support arm, and an adjustment device coupled to at least one of said upper and lower support arms for allowing adjustment of an angle between said support arm and associated leg cuff.

9. An orthopedic knee brace, comprising:

an upper leg cuff mountable above the knee of a wearer;

a lower leg cuff mountable below the knee of the wearer, an upper support arm extending from said upper leg cuff;

a lower support arm extending from said lower leg cuff; and a hinge assembly disposed between said upper and lower leg cuffs, said hinge assembly comprising a first gear member having gear teeth on a portion thereof, said first gear member coupled for rotation with said upper support arm and having an articulation surface communicating with a corresponding surface of said upper support arm, and a second gear member having gear teeth intermeshing with said gear teeth of said first gear member, said second gear member coupled for rotation with said lower support arm and having an articulation surface communicating with a corresponding surface of said lower support arm;

wherein said knee brace is configured to allow a predetermined degree of medial/lateral articulation of said upper and lower support arms while maintaining relative coplanarity of said first and second gear members.

10. The orthopedic knee brace of claim 9, further comprising an adjustment device coupled to at least one of said upper and lower support arms for allowing adjustment a torsional force applied to said at least one support arm whereby said at least one support arm may be urged into engagement with the knee of a wearer.

11. The orthopedic knee brace of claim 10, wherein said adjustment device comprises:

a first part coupled to said at least one support arm;

a second part coupled to said associated leg cuff;

a torsion spring mounted to one of said first and second parts;

a shaft extending through said torsion spring and having first and second ends rotatably mounted to the other of said first and second parts;

a driven gear engaging said shaft and said torsion spring; and a drive gear engaging said driven gear and the other of said first and second parts, rotation of said drive gear causing said torsion spring to coil, thereby changing an angle between said first and second parts.

12. The orthopedic knee brace of claim 9, further comprising an adjustment device coupled to at least one of said upper and lower support arms for allowing adjustment of an angle between said at least one support arm and associated leg cuff.

13. The orthopedic knee brace of claim 12, wherein said adjustment device comprises:

a hinge pin having first and second hinge portions rotatably mounted thereon, said first hinge portion being coupled to said at least one support arm and said second hinge portion being coupled to said associated leg cuff;

an arch bar extending over said hinge pin from said first portion to said second portion, said arch bar movably coupled at its ends to said first and second hinge portions; and an adjustment screw threadingly engaging said hinge pin and said arch bar, rotation of said screw causing a distance between said hinge pin and said arch bar to vary, thereby changing an angle between said first and second hinge portions.

14. A hinge assembly for an orthopedic knee brace having upper and lower support arms, said hinge assembly comprising:

a hinge support;

a first gear member pivotally connected to said hinge support, said first gear member coupled for rotation with said upper support arm and having an articulation surface adapted to communicate with a surface of said upper support arm; and a second gear member pivotally connected to said hinge support, said second gear member coupled for rotation with said lower support arm and having an articulation surface adapted to communicate with a surface of said lower support arm, wherein said hinge assembly is configured to allow a predetermined amount of articulation of said upper and lower support arms in a plane substantially perpendicular to a plane of rotation of said first and second gear members.

15. The hinge assembly of claim 14, wherein said first gear member has a first recessed area for receiving an end of said upper support arm, said first recessed area having a shape generally corresponding with a shape of an end of said upper support arm, and said second gear member has a second recessed area for receiving an end of said lower support arm, said second recessed area having a shape generally corresponding with a shape of an end of said lower support arm.

16. The hinge assembly of claim 14, wherein said first and second recessed areas are at least partially defined by said articulation surfaces.

17. An orthopedic knee brace incorporating the hinge assembly of claim 14, said knee brace comprising an upper leg cuff coupled to said upper support arm, a lower leg cuff coupled to said lower support arm, and an adjustment device coupled to at least one of said upper and lower support arms for allowing adjustment of an angle between said support arm and associated leg cuff.

* * * * *

UNITED STATES PATENT AND TRADEMARK OFFICE
CERTIFICATE OF CORRECTION

PATENT NO. : 6,527,733 B1
DATED : March 4, 2003
INVENTOR(S) : Ceriani et al.

It is certified that error appears in the above-identified patent and that said Letters Patent is hereby corrected as shown below:

Column 11,
Line 63, please change "binge" to -- hinge --.

Column 12,
Line 3, please change "rackidly" to -- rackingly --.

Signed and Sealed this

Twenty-third Day of December, 2003

JAMES E. ROGAN
*Director of the United States Patent and Trademark Office*